(12) United States Patent
Alzain et al.

(10) Patent No.: US 10,492,895 B1
(45) Date of Patent: Dec. 3, 2019

(54) FACEBOW WITH DOUBLE BITE FORKS

(71) Applicant: KING SAUD UNIVERSITY, Riyadh (SA)

(72) Inventors: Sahar Asaad Alzain, Riyadh (SA); Ohood Turkistani, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/120,132

(22) Filed: Aug. 31, 2018

(51) Int. Cl.
*A61C 19/045* (2006.01)

(52) U.S. Cl.
CPC .................................. *A61C 19/045* (2013.01)

(58) Field of Classification Search
CPC ...... A61C 19/045; A61C 19/05; A61C 19/055
USPC .............................................. 433/73, 68, 69
See application file for complete search history.

(56) References Cited

U.S. PATENT DOCUMENTS

| | | | |
|---|---|---|---|
| 2,334,898 A | 11/1943 | Bigger et al. | |
| 2,418,648 A | 4/1947 | Kile | |
| 2,562,106 A | 7/1951 | Leathers | |
| 2,814,876 A | 12/1957 | Stuart | |
| 3,206,852 A * | 9/1965 | Swanson | A61C 11/022 433/56 |
| 3,643,332 A | 2/1972 | Lee | |
| 4,836,779 A * | 6/1989 | Beu | A61C 19/045 433/73 |
| 8,556,626 B2 | 10/2013 | Evenson | |
| 2009/0246729 A1* | 10/2009 | Massad | A61C 19/05 433/71 |
| 2015/0147726 A1* | 5/2015 | Filtchev | A61C 1/0015 433/213 |
| 2017/0128180 A1* | 5/2017 | Palaskar | A61C 19/045 |
| 2017/0165042 A1 | 6/2017 | Hillukka et al. | |

FOREIGN PATENT DOCUMENTS

WO 2016196335 A1 12/2016

\* cited by examiner

*Primary Examiner* — Yogesh P Patel
(74) *Attorney, Agent, or Firm* — Richard C. Litman; Nath, Goldberg & Meyer

(57) ABSTRACT

The facebow with double bite forks uses two bite forks. The bite forks are connected to one common handle of the bite fork secured to the facebow frame. The assembly for the two bite forks helps to maintain a predetermined vertical distance of 1.5 centimeters between them. An infraorbital pointer is also attached to the facebow frame. It is secured in place to act as the anterior reference point. The adjustable earpieces inserted into the patient's external auditory meatuses are adjusted to be considered as posterior reference points. This assembly helps to record the facebow and centric relation positions simultaneously.

2 Claims, 3 Drawing Sheets

FACEBOW WITH DOUBLE BITE FORKS

BACKGROUND

1. Field

The present disclosure relates to a facebow with double bite forks for making the facebow record and the centric relation record simultaneously in cases of maxillary and mandibular complete dentures.

2. Description of the Related Art

Proper setting of artificial teeth is the result of an understanding of how the maxillary and mandibular teeth articulate together. This is typically performed using a mechanical device called an articulator in conjunction with mounted models (casts). The articulator represents the temporomandibular joints and jaws to which maxillary and mandibular casts are attached to simulate mandibular movement. The articulator helps to maintain the maxillo-mandibular relationship of the casts during tooth arrangement. Therefore, dental casts are mounted on an articulator to reproduce the location and movement of the lower teeth and mandible relative to the upper teeth and maxilla.

A facebow is a dental instrument used to record the relationship of the maxillary arch to anatomic reference points such as the mandibular condyles, transverse horizontal axis and one anterior point and then transfers this relationship to an articulator. In addition to establishing facebow record, jaw relation should also be recorded. Jaw relation is the position of the mandible relative to the maxilla. It is extremely important to register both facebow and jaw relation to be able to construct dentures.

In dentulous or partially dentulous patients, the existing natural teeth are used to make imprints on a wax sheet that is attached to a single bite fork. However, in edentulous patients, an occlusal wax rim is fabricated and is used instead of teeth in facebow and centric relation recordings. In all clinical cases, the bite fork is mounted on the bow part of the facebow.

In both dentulous and edentulous cases, mounting of the maxillary cast is done using a facebow record, whereas the mandibular cast is mounted using a centric occlusion relation record. Clinically, both facebow and centric occlusion relation are recorded separately most of the time, and then transferred to the articulator for mounting the maxillary and mandibular casts. Thus, a facebow with double bite forks solving the aforementioned problems is desired.

SUMMARY

The facebow with double bite forks uses two bite forks. Both bite forks are introduced with a predetermined separation vertical distance of 1.5 centimeters between them. Each bite fork is designated for each arch. The standard bite fork of a conventional facebow is inserted into the upper occlusal wax rim of the maxillary record block. The introduced additional or lower bite fork is located below the standard one and is connected to the handle of the standard bite fork by a vertically oriented connector. The lower bite fork is attached to the occlusal wax rim of the mandibular record block. Both bite forks are connected by one common handle of the face bow. The handle of the bite fork is then connected to the facebow frame and secured. An infraorbital pointer is also attached to the facebow frame. It is secured in place to act as the anterior reference point. The adjustable earpieces are inserted into the patient's external auditory meatuses and are considered as posterior reference points. This assembly helps to record the facebow and centric relation position simultaneously.

Features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The facebow with double bite forks is able to record both facebow and centric relation records simultaneously using the double bite forks. The standard upper bite fork is inserted into the occlusal wax rim of the maxillary record block and the additional lower bite fork (located below the standard bite fork) is inserted into the occlusal wax rim of the mandibular record block.

The disclosure introduces an additional bite fork that is located below the standard bite fork of the conventional facebow. Therefore, two bite forks are provided, one designated for each arch. The vertical distance between the two bite forks is predetermined and is 1.5 centimeters.

Figure 1:
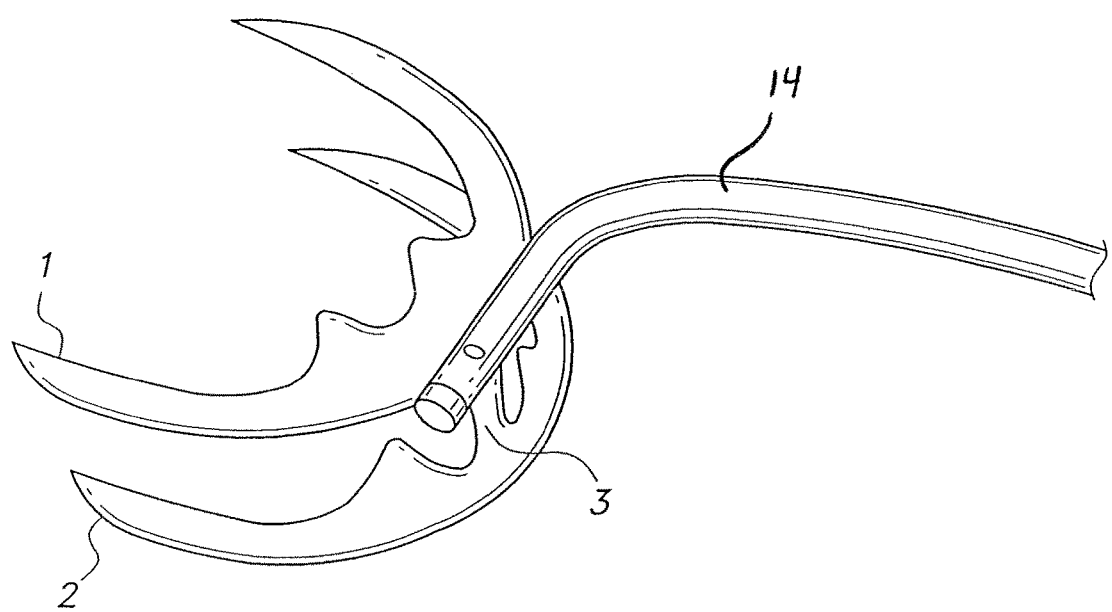
FIG. 1 is a perspective view of double bite forks of the facebow with double bite forks described herein; the bite forks are connected to one common handle of the facebow.

FIG. 1 is a perspective view illustrating an upper bite fork 1 and a lower bite fork 2. The upper bite fork 1 corresponds to a standard bite fork of a conventional facebow. The upper bite fork 1 is usually inserted into the upper occlusal wax rim of the maxillary record block. The lower bite fork 2 is introduced and is connected to the handle of the bite fork 14 by a vertically oriented connector 3. The lower bite fork 2 is inserted into the occlusal wax rim of the mandibular record block. The double bite fork handle 14 is connected to the facebow, as described below.

Figure 2:
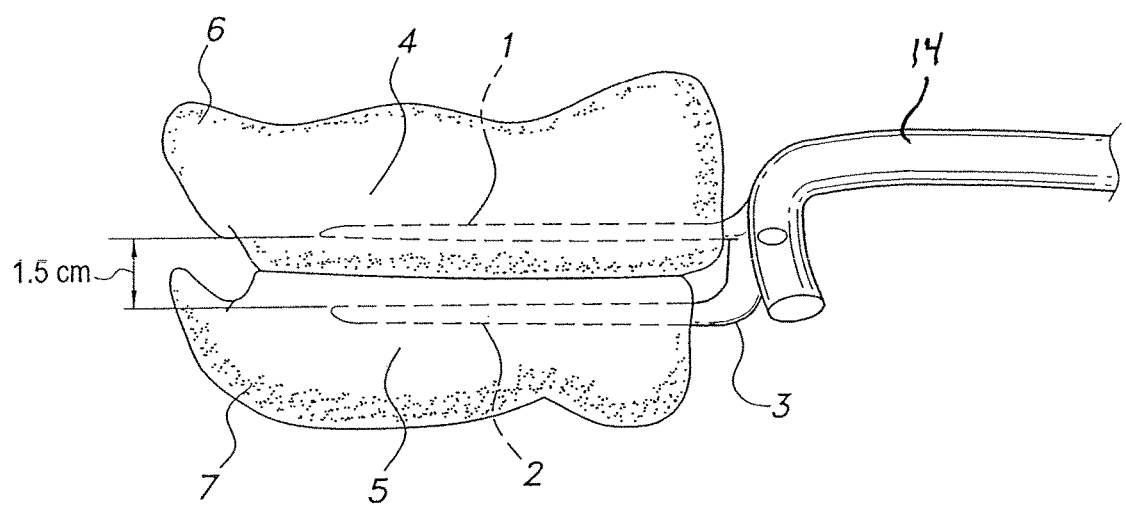
FIG. 2 is a perspective view showing the double bite forks of FIG. 1 inserted into maxillary and mandibular record blocks.

FIG. 2 is a perspective view showing the double bite forks 1 and 2 inserted into maxillary and mandibular occlusal wax rims 4, 5 of the maxillary and mandibular record blocks 6, 7, respectively. The occlusal wax rims 4, 5 of the maxillary record block 6 and the mandibular record block 7 are adjusted, and the vertical dimension and centric relation position are established and verified. The record blocks 6, 7 are placed in the patient's mouth; the double bite forks 1, 2 are then warmed and inserted into their respective occlusal wax rims 4, 5. The upper warm bite fork 1 is inserted into the occlusal wax rim 4 of the maxillary record block 6, and the lower warm bite fork 2 is inserted into the occlusal wax rim 5 of the mandibular record block 7. The vertically oriented connector 3 connects lower bite fork 2 to the handle of the bite fork 14 at its center. Therefore, both the upper and lower bite forks 1, 2 are inserted into their respective occlusal wax rims 4, 5 to record the facebow and centric relation records simultaneously in one step.

Figure 3:
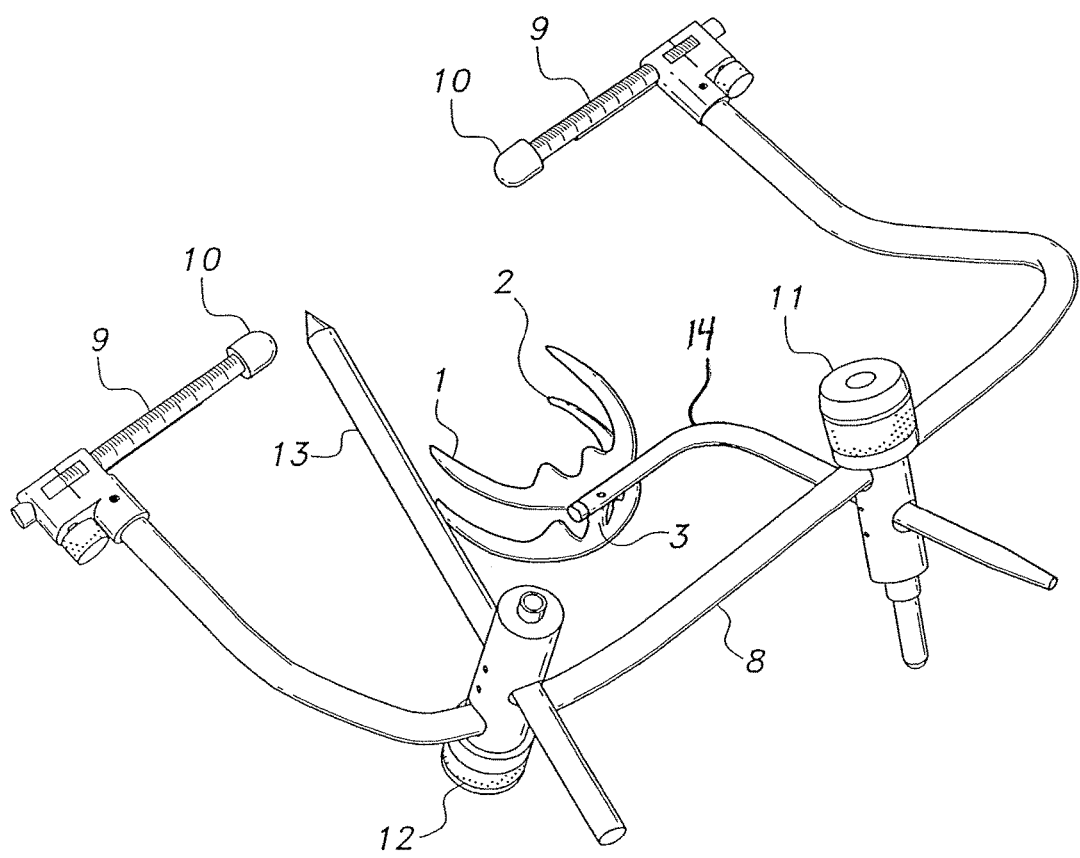
FIG. 3 is a perspective view of the assembly of a facebow with double bite forks.

FIG. 3 is a view illustrating the assembly of the different parts of the facebow with double bite forks, including the bite forks 1 and 2, the u-shaped frame 8, the condylar rods 9 and earpieces 10, the locking devices 11, 12 and the infraorbital pointer 13. The lower bite fork 2 is connected to the bite fork handle 14 by the vertically oriented connector 3. The bite fork handle 14 is inserted into the u-shaped frame 8 and is secured in position by the locking device 11.

The earpieces 10 are the terminal extensions of the condylar rods 9 and are adjustable. Adjustments should be made by positioning the earpieces 10 into the patient's external auditory meatuses that are considered as posterior reference points. Similar readings should be established on both condylar rods 9 to assure symmetry. The anterior reference point is the infraorbital pointer 13 that is related to the infraorbital notch.

The facebow with double bite forks overcomes the drawbacks of introducing an interocclusal recording material. An introduced material may undergo distortion that can adversely affect the accuracy of the facebow and centric relation records. The facebow with double bite forks also reduces the clinical chairside time by simultaneously recording both the facebow and the centric relation records in one step using the same device.

It is to be understood that the facebow with double bite forks is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A facebow with double bite forks for making a facebow record and a centric relation record simultaneously of an edentulous patient, comprising:
   a u-shaped frame, wherein the u-frame defines a horizontal plane;
   two horizontally adjustable condylar rods located at the ends of the u-shaped frame and two earpieces extending from the rods and adapted to be inserted into the patient's external auditory meatuses, wherein the earpieces act as posterior reference points;
   two locking mechanisms mounted on the u-shaped frame;
   an infraorbital pointer slidably adjustable and securable to the u-shaped frame by one of the two locking mechanisms, wherein the slidable infraorbital pointer acts as an anterior reference point;
   a bite fork handle slidably adjustable and securable to the u-shaped frame by the other of the two locking mechanisms; and
   a double bite fork assembly attached to the bite fork handle, the assembly consisting of:
      an upper U-shaped bite fork adapted to be inserted into an occlusal wax rim of a maxillary record block;
      a lower U-shaped bite fork adapted to be inserted into an occlusal wax rim of a mandibular record block; and
      a vertically oriented connector with respect to the horizontal plane connecting the lower bite fork to the handle of the bite fork, wherein the upper bite fork and the lower bite fork are separated vertically by a fixed dimension of 1.5 centimeters;
   wherein the facebow with double bite forks is capable of obtaining a facebow record and a centric relation record simultaneously.

2. The facebow with double bite forks according to claim 1, wherein each said bite fork may be inserted into the wax rim of the corresponding arch, with the vertically oriented connector connecting the lower bite fork to the bite fork handle.

\* \* \* \* \*